Figure 1:
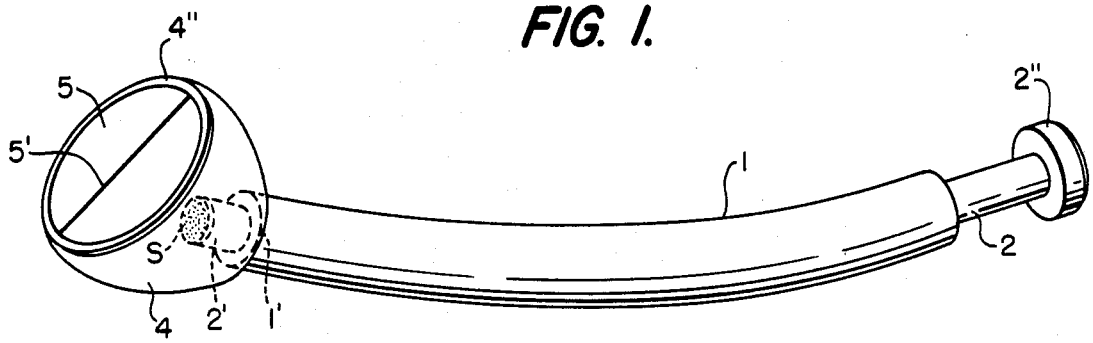

United States Patent [19]

Kosasky

[11] Patent Number: 4,628,941
[45] Date of Patent: Dec. 16, 1986

[54] INSTRUMENT AND PROCESS FOR SAMPLING CERVICAL MUCUS AND THE LIKE

[76] Inventor: Harold Kosasky, 225 Woodland Rd., Chestnut Hill, Mass. 02167

[21] Appl. No.: 780,236

[22] Filed: Sep. 25, 1985

Related U.S. Application Data

[63] Continuation of Ser. No. 597,682, Apr. 6, 1984, abandoned.

[51] Int. Cl.⁴ .............................................. A61B 10/00
[52] U.S. Cl. .................................................... 128/759
[58] Field of Search ............................. 128/127–129, 128/132, 749, 751, 759

[56] References Cited

U.S. PATENT DOCUMENTS

| 2,616,421 | 11/1952 | Greenberg | 128/749 |
| 4,013,066 | 3/1977 | Schuster | 128/2 |
| 4,131,112 | 12/1978 | Kopito et al. | 128/2 |
| 4,157,709 | 5/1977 | Schuster et al. | 128/759 |

FOREIGN PATENT DOCUMENTS

| 109229 | 4/1928 | Austria | 128/127 |
| 222 | of 1886 | United Kingdom | 128/131 |

OTHER PUBLICATIONS

Observations on the Anatomy of the Rectovaginal Pouch and Septum by R. J. P. Kuhn et al.: Obstetrics & Gynecology, vol. 59, No. 4, Apr. 1982.

Primary Examiner—Kyle L. Howell
Assistant Examiner—David Shay
Attorney, Agent, or Firm—Rines and Rines, Shapiro and Shapiro

[57] ABSTRACT

A cervical mucus extractor embodying a semi-flexible hemispherical cup carried at the end of a tube for insertion into the vagina to position the cup over the cervix, with a plunger extending coaxially within the tube and terminating in a tip that, by operation of the plunger, is inserted through the cup into contact with cervical mucus, the same being removable therefrom to extract the desired sample of such mucus, as for testing.

3 Claims, 2 Drawing Figures

INSTRUMENT AND PROCESS FOR SAMPLING CERVICAL MUCUS AND THE LIKE

This is a continuation application of Ser. No. 597,682 filed Apr. 6, 1984, now abandoned.

The present invention relates to improvements in instruments and processes for sampling cervical mucus and similar applications, being more particularly directed to vaginal insert instruments that can be used by the woman herself to obtain a sample of cervical mucus for examination, including for viscosity measurements thereof that provide ovulation time and other information.

While it has generally heretofore required skilled medical personnel to retrieve specimens of cervical mucus, and the like, attempts have been made to provide probes useable by the woman herself to obtain such samples for such purposes as performing tests upon the same at home as, for example, for the determination of ovulation time, above mentioned. My co-invention of one such device is described in U.S. Pat. No. 4,157,709, embodying a vaginal probe provided with a locating tongue or foot that requires positioning with the aid of an inserted finger to reach the posterior fornix, following which a universal-angle shaft is projected to contact, hopefully, cervical mucus, assuming the uterus is not tipped backward. The disadvantages of the requirement for finger insertion and location, the lack of utility with backwardly tilted cervices, and the fact that the angled shaft is not actually universal because of wide variations in anatomical dimensions and form, have, however, rendered this type of probe less useful than at first expected.

It is to the obviating of these and other disadvantages of prior instruments of this character that the present invention is primarily directed; it being an object of the invention to provide a new and improved vaginal instrument and process, adapted for self-use by the woman, for retrieving cervical mucus samples, and for accomplishing the same without the need for finger insertion and manipulation, with extreme sureness of application and location, and with effective utilization irrespective of uteral tipping and dimensions or anatomical variations.

A further object is to provide a novel cervical mucus or similar extractor of more general utility, as well.

Other and further objects will be explained hereinafter and are more particularly delineated in the appended claims.

In summary, however, from one of its important aspects, the invention embraces an instrument for insertion into the vagina for the removal of a sample of cervical mucus fluid having, in combination, a cylindrical tube curved and shaped for insertion within the vagina and having an internal coaxially slidable plunger terminating at its inner end in a tip carrying a surface that, when contacting mucus, will cause the same to adhere to the surface, and terminating at its outer end in a grip that enables insertion and withdrawal of the plunger into and from the tube, the plunger being flexible to conform to the curve of the tube in successive positions of insertion and withdrawal; a substantially hemispherical cup having an opening at its bottom connected to the inner end of the tube and a flexible cover disposed over the cup provided with slot means normally closed to prevent the introduction of vaginal fluids during insertion over the cervix with the plunger tip extending through the opened slot means; the rim of the cup being proportioned to receive and circumscribe the cervix such that the plunger tip passing through the opened slot means enables its surface to adhere cervical mucus from the central region of the cervix, the pulling outward of the plunger grip removing the plunger and its mucuscovered surface from the tube for the testing of the mucus. Preferred details and best mode embodiment are hereinafter presented.

Figure 2:
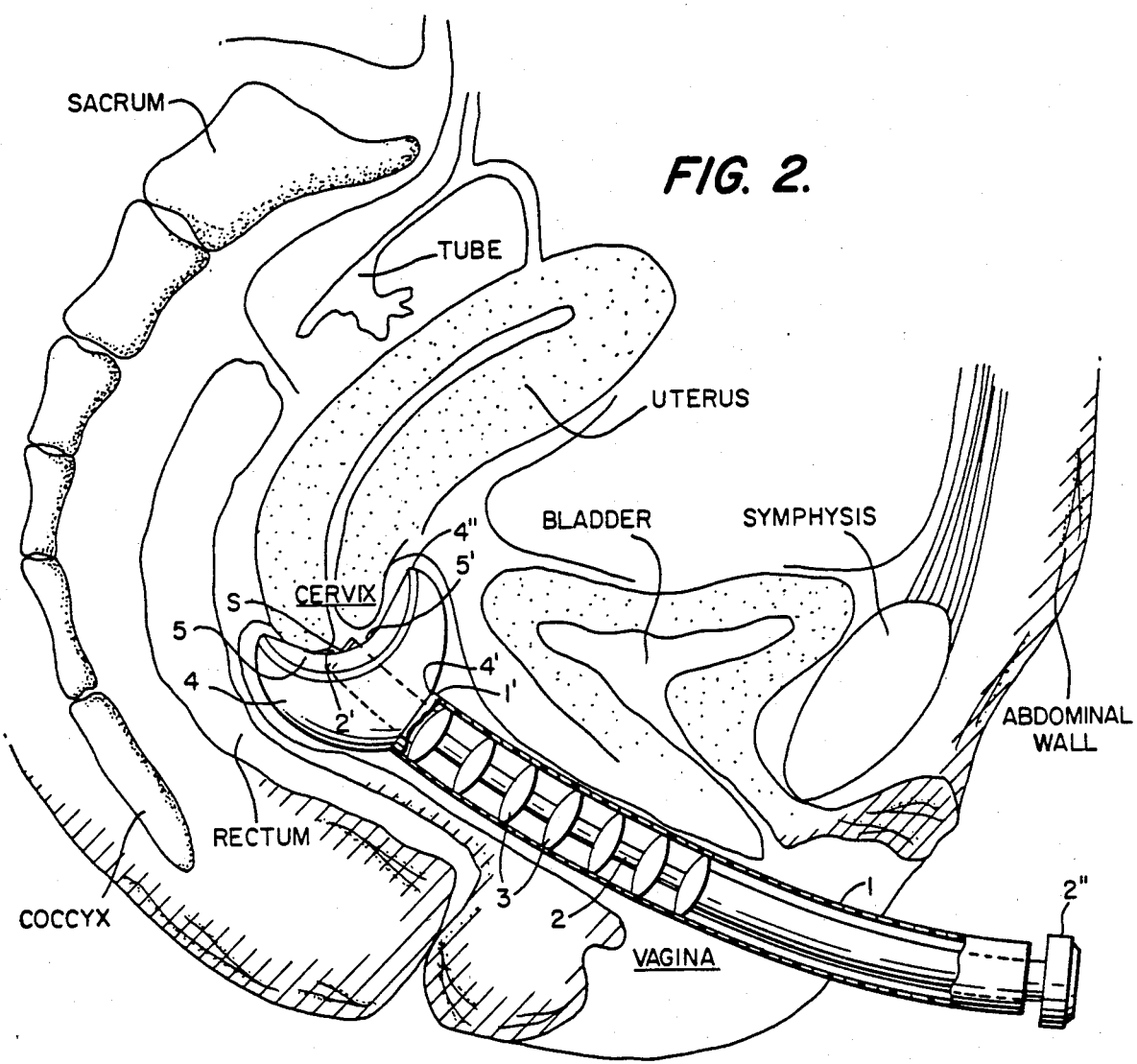

The invention will now be described with reference to the accompanying drawing;

FIG. 1 of which is a perspective view of an instrument constructed in accordance with a preferred embodiment of the invention, FIG. 2 of which is a partially sectional view showing the instrument in operation to obtain a sample of cervical mucus.

Referring to the drawing, the instrument is shown comprising a hollow cylindrical tube 1, as of rigid or semirigid plastic and the like, curved and shaped somewhat to conform to the vaginal walls so as to permit ready insertion of the same upward toward the cervix, so labelled. Removably inserted into the tube 1 is a coaxially movable plunger 2 of relatively flexible plastic or the like to permit its conformance with the shape of the tube 1 at all positions of insertion and withdrawal therein and therefrom—the overall length of the plunger being greater than that of the tube 1 so that the inner end carrying the plunger tip 2' may be inserted to extend through and beyond the inner end 1' of the tube 1. At its outer end, the plunger 2 may be provided with a knob grip or handle 2" to facilitate insertion and withdrawal, and the plunger may be provided with a plurality of longitudinally spaced disc locators 3 to assist in the alignment of the plunger action at all positions of insertion or withdrawal.

In accordance with the invention, the inner end 1' of the tube 1 is secured to and enters into an opening 4' in the bottom of a substantially hemispherical cup 4, as of semi-rigid, somewhat flexible thin-walled plastic such as polyethelene or the like, of diameter several times that of the tube 1, as later explained. The plunger tip 2', when the plunger is fully or near-fully inserted into the tube 1, may extend a substantial distance along the radius of the cup 4 toward its outer rim 4".

Secured over the cup rim 4" is a flexible cover 5, slotted at 5' to permit the reception of the cervix into the cup 4 upon insertion of the cup over the cervix. Upon inserting the cup over the cervix, the cervix pushes the cover 5 inward into the cup and thereby opens the slot 5' of the flexible cover 5 so that the plunger tip 2' may be brought into contact with cervical mucus in the central region of the cervix as thus received in the cup 4, as will be appreciated from the drawing. The end of the plunger tip 2' is provided with a surface S, such as a roughened plate, as of ground glass or the like, to which the cervical mucus will adhere on contact, enabling withdrawal of the plunger 2 to enable removal of a mucus sample on the surface S. During insertion into the vagina, the cover 5 is closed preventing contact by the plunger tip 2' and its surface S with unwanted vaginal fluids.

Since the mean depth of the rectovaginal pouch (5.3 cm.) and the mean length of the rectovaginal septum (2.1 cm.) are neither altered by parturition or prolapse ("Observations on the Anatomy of the Rectovaginal Pouch and Septum", Kuhn & Hollyock, Obstetrics & Gynacology, Vol. 59, No. 4, April, 1982 p. 445-6), a standard instrument can be provided, with the woman fitted only for size of the cervical cup or cap 4. The instrument tube 1 may measure 12 cm. and aligns with the longitudinal axis of the vagina. The cervical cup or cap 4 may measure approximately 2.5 cm. in depth with a rim diameter of 4.5 cm. By lining up the cervical cup or cap, its rim 4" contacts the cervix and surrounds it. If the cup 4 does not surround and encapsulate the cervix, it will be neither comfortable nor fit in the vagina at the proper distance and the cover slot 5' of the cup 4 will not open. When the cervix is received in the cup 4, then the plunger 2 is pushed home after the cup 4 has totally contacted the cervix adhering aligned central cervix mucus to the plunger tip surface S. The plunger is then partially withdrawn 3 to 4 cm to disengage from the mucus and then the entire instrument is removed from the vagina. The mucus sample carried at S may then be inserted into any desired viscosity reading instrument to determine the degree of thickness or thinness of the cervical mucus, for example, or for other examination or measurement.

One of the features of advance of this instrument over previous instruments, as before described, is the attachment of the cervical cup 4 to the front end rather than employing finger-adjusting tongues to line up the instrument with the posterior fornix, or the area behind the cervix. Current estimates are that the cervical cup 4 will "line up" the cervix with the plunger accurately in over 90% of patients. This instrument will be fitted in the size of the cup 4 by the physician. The instrument is equally suitable for those women whose uteruses are tilted backwards (retroverted) or are tilted forward (anteverted) in the usual fashion, unlike the previous introducer containing the tongue.

Further modifications will occur to those skilled in this art and such are considered to fall within the spirit and scope of the invention as defined in the appended claims.

What is claimed is:

1. An instrument for insertion into the vagina for the removal of a sample of cervical mucus fluid, comprising, in combination, a cylindrical tube curved and shaped for insertion within the vagina; a plunger coaxially slidable within the tube, the plunger terminating at its inner end in a tip carrying a surface to which mucus will adhere on contact and terminating at its outer end in a grip that enables insertion and withdrawal of the plunger into and from the tube, the plunger further being flexible to conform to the curve of the tube in successive positions of insertion and withdrawal; a substantially hemispherical cup connected at its bottom to the inner end of the tube, the bottom of the cup having an opening in communication with an opening at the inner end of the tube to provide communication between the respective interiors of the cup and the tube; and a flexible cover disposed over the cup and secured over the rim of the cup, the cover being provided with slot means normally closed to prevent the introduction of vaginal fluids during insertion of the tube but adapted to open by the cover being pushed inward into the cup in response to insertion of the cup over the cervix, the rim of the cup being proportioned to receive and circumscribe the cervix such that the plunger tip may pass through the opened slot means for contacting the surface of the plunger tip with cervical mucus from the central region of the cervix, whereby the pulling outward of the plunger grip effects removal of the plunger and its mucus-covered tip surface from the tube for the testing of the mucus.

2. An instrument as claimed in claim 1 and in which said plunger tip surface comprises a roughened plate.

3. A process for removing a sample of cervical mucus from the central region of the cervix, that comprises, inserting a substantially hemispherical cup having a flexible cover secured over its rim into and along the vagina, the cover having a normally closed slot, inserting the cup over the cervix to push the cover inward into the cup and thereby open the slot to expose the cervix to the interior of the cup, introducing a sampling surface through an opening in a bottom portion of the cup to contact mucus at the central region of the cervix and adhere said mucus to said surface, partially withdrawing the surface, and fully withdrawing the cup back out of the vagina to recover the adhered mucus sample.

* * * * *